(12) United States Patent
Hommann et al.

(10) Patent No.: US 7,654,987 B2
(45) Date of Patent: Feb. 2, 2010

(54) ADMINISTERING DEVICE WITH A PROTECTIVE CAP REMOVING DEVICE AND A NEEDLE PROTECTING SLEEVE LOCKING MEANS

(75) Inventors: Edgar Hommann, Grossaffoltern (CH); Benjamin Scherer, Uster (CH)

(73) Assignee: TecPharma Licensing AG, Burgdorf (CH)

( * ) Notice: Subject to any disclaimer, the term of this patent is extended or adjusted under 35 U.S.C. 154(b) by 795 days.

(21) Appl. No.: 10/925,888

(22) Filed: Aug. 25, 2004

(65) Prior Publication Data

US 2005/0049561 A1 Mar. 3, 2005

(30) Foreign Application Priority Data

Aug. 28, 2003 (DE) ................. 103 39 794

(51) Int. Cl.
*A61M 5/00* (2006.01)
(52) U.S. Cl. ..................... 604/263; 604/243
(58) Field of Classification Search ............... 604/208, 604/197, 148, 134–136, 131, 232, 234, 181, 604/187, 241–243, 192, 195, 198, 263
See application file for complete search history.

(56) References Cited

U.S. PATENT DOCUMENTS 6,221,044 B1 * 4/2001 Greco ................. 604/134
6,258,068 B1 * 7/2001 Kirchhofer et al. .......... 604/208
6,585,702 B1 * 7/2003 Brunel ................. 604/263
2005/0261634 A1 * 11/2005 Karlsson ................ 604/197

FOREIGN PATENT DOCUMENTS

DE 84 26 817.4 7/1985
EP 0 456 964 B1 11/1991
EP 0 518 397 B1 2/1996

* cited by examiner

*Primary Examiner*—Matthew F Desanto
(74) *Attorney, Agent, or Firm*—Dorsey & Whitney LLP; David E. Bruhn, Esq.

(57) ABSTRACT

A device for administering an injectable product including a casing, an injection mechanism including an injection needle pointing in an insertion direction, and a protective cap for the injection needle wherein, in one embodiment, the administering device includes a removing device for removing the protective cap from the injection needle and, in another embodiment, the administering device includes a needle protecting sleeve shiftable generally in alignment with the casing and generally between a front position, advanced relative to the casing, for protecting the injection needle and to a rear position, retracted relative to the casing, for inserting the injection needle into a tissue. In one embodiment, the needle protecting sleeve is prevented from moving completely into the rear position by a lock when the protective cap is protecting the injection needle.

14 Claims, 2 Drawing Sheets

ADMINISTERING DEVICE WITH A PROTECTIVE CAP REMOVING DEVICE AND A NEEDLE PROTECTING SLEEVE LOCKING MEANS

BACKGROUND

The present invention relates to a device for administering an injectable product, in particular an injection pen for fluid products such as insulin, which comprises features for protecting an injection needle associated with the administering device. The application claims the priority of German patent application No. 103 39 794.9, filed on Aug. 28, 2003 with the German Patent and Trademark Office.

Administering devices such as injection pens are widely used in medical or therapeutic treatment in which an injectable product has to be repeatedly administered. In the case of diabetes, for example, it is necessary to administer an insulin dosage to the patient at regular intervals. Injection pens for this purpose are designed to be reusable. For each injection, however, a new needle or needle unit with a new, sterile injection needle has to be attached to the administering device. In order, for example, to avoid pricking injuries when removing and attaching a needle unit, and to ensure the sterility of the injection needle, the injection needle is typically surrounded by a protective cap which is placed over the injection needle or needle unit. In order to use the injection pen, the protective cap is generally removed from the injection needle using an aid. In order to further avoid exposing the injection needle, even when the protective cap has been removed, a protective means for protecting the exposed injection needle can be provided on the administering device. The protective means can, for example, be formed by a needle protecting sleeve which surrounds the injection needle in a front position, advanced relative to the casing, and exposes the injection needle in a rear position, shifted backwards relative to the casing.

For administering an injectable product quickly and easily, it is cumbersome to have to carry along a separate aid for removing a protective cap from the injection needle. Furthermore, administering the injectable product quickly and easily can be compromised, since due to the protective means, it is not possible to recognize whether the protective cap has been placed on the injection needle or not.

SUMMARY

It is therefore an object of the present invention to provide a device for administering an injectable product, in which a protective cap can be easily and quickly removed from an injection needle, an injection needle is protected at all times against pricking injuries, the presence of a protective cap over an injection needle can be easily recognized, and the sequence of the procedures of removing the protective cap and inserting the injection needle are coordinated or adjusted to each other.

The object is addressed by the present invention which provides a device for administering an injectable product, comprising a casing, an injection means including an injection needle pointing in the insertion direction, and a protective cap which can be placed onto the injection needle, wherein a removing device for removing the protective cap from the injection needle is arranged on or in the casing. In one embodiment, the present invention comprises a device for administering an injectable product, comprising a casing, an injection means including an injection needle pointing in the insertion direction, a protective cap which can be placed onto the injection needle, and a needle protecting sleeve which can be shifted along the casing and which is in a front position, advanced relative to the casing, in order to protect the injection needle and can be moved to a rear position, retracted relative to the casing, when inserting or in order to insert the injection needle into a tissue, wherein when the protective cap is attached, the needle protecting sleeve is prevented from retracting completely into the rear position by a locking means.

In accordance with a first aspect of the present invention, a device for administering an injectable product, in one preferred embodiment an injection pen, comprises a casing, an injection means to which an injection needle is connected to and aligned in the insertion direction along the longitudinal axis of the casing, and a protective cap which can be placed onto the injection needle. The protective cap serves to protect the injection needle when, for example, it is attached to the administering device for an injection. The protective cap also serves to protect the user from pricking injuries. In accordance with the invention, a removing device for removing the protective cap from the injection needle is arranged on or in the casing of the administering device. The removing device can thus lie substantially in the interior of the casing and be partially accessible from without, or it can be arranged mostly on an outer region of the casing. The removing device can be moved relative to the casing in order to remove the protective cap from the injection needle or from a needle unit arranged on the injection means.

In an administering device comprising a removing device in accordance with the invention, no additional aid is needed in order to remove the protective cap from the injection needle. A number of individual parts are therefore not required in order to administer a product, but rather the administering device is already operable. Furthermore, the removing device enables the protective cap to be easily removed from the injection needle.

In a preferred embodiment of the invention, the removing device is formed by a sleeve which can be shifted along the longitudinal axis of the casing and can be pushed over a cylindrical protective cap and which comprises on its inner area a latching means which engages with the protective cap. In order to remove the protective cap from the injection needle, the removing device is pushed from a front position, advanced relative to the casing, along the longitudinal axis, to a rear position, retracted relative to the casing. In the rear position, the latching means latches in or connects to the protective cap. By advancing the sleeve into the front position, the protective cap can be removed, since it is fixed relative to the sleeve due to the latch.

The latching means on the removing device can, for example, be formed by at least one, preferably two or three, gripping arm or arms protruding inwards and engaging with a resistor on the removing device, in order to latch. Advantageously, a gripping arm protrudes obliquely forward in the insertion direction into the interior of the casing, towards the protective cap. It is, for example, possible to arrange gripping arms on a sleeve as the removing device in such a way that they abut a circumferential area of a cylindrical protective cap and are elastically biased. In order to remove the protective cap, the sleeve is shifted counter to an insertion direction of the administering device, until the gripping arms reach a rim, i.e. the facing side of the sleeve pointing inwards into the casing, at the end of the sleeve and are moved radially inwards by the bias and thus lie opposite the rim or facing side of the sleeve. With the gripping arms in this position, the rim forms a resistor for the gripping arms, such that the sleeve and the protective cap are latched to each other when moving in the insertion direction. If the sleeve is shifted in the insertion direction, relative to the casing, into a front position, it thus pushes the protective sleeve from the injection needle due to the gripping arms engaging with the rim of the sleeve.

In order to shift the sleeve relative to the casing, engagers can, for example, be provided, at which a user can engage and guide the sleeve. The engagers can, for example, protrude outwards from the casing through slits running in the longitudinal direction or can be arranged on a part of the sleeve which protrudes beyond the casing in an extension of the casing. Other possible engagements are of course also conceivable, in order to arrange the sleeve such that it can be shifted relative to the casing. Besides the rim of the sleeve, a step, heel or other suitable surface profile can also be provided, as a resistor for the at least one gripping arm, on the circumferential area of the protective cap. Instead of a gripping arm, a corresponding surface profile on an inner circumference of the sleeve, such as, for example, a ribbed, serrated or stepped grating, can be provided. It is also conceivable to provide an elastic rubber element in the inner circumference of the sleeve which is compressed when the sleeve is retracted, until it expands on an abutment on the sleeve, such as, for example, a groove, and therefore latches the sleeve to the protective cap.

In principle, a removing device in accordance with the present invention can also be provided by changing the position of the functional elements provided on the removing sleeve and the protective cap. That is to say, gripping arms or other latches may be provided on the protective cap and cooperate with a resistor on the removing device. It is, however, advantageous if no particular means for the removing device are needed on the protective cap, since conventional protective caps, existing as mass-produced goods, can then be used.

In order to further facilitate the procedure of removing the protective cap from the injection needle, in one embodiment it is possible to provide a biasing element, for example, between the protective cap and the casing, which is biased from the front position to the rear position, against a force, when the removing device is retracted. For this purpose, a common spiral spring may, for example, serve, which is compressed when the removing device is retracted. If the force for retracting the removing device abates, e.g., if sleeve is released, it is advanced relative to the casing by the biasing element, into the advanced position, and the needle protecting cap is thus removed with it, wherein the spring is relaxed. In this embodiment, the spring force of the spiral spring is to be adjusted to the force with which the protective cap is fixed on the injection needle.

In one embodiment, the present invention comprises a device for administering an injectable product including a casing, an injection mechanism including an injection needle pointing in an insertion direction, and a protective cap for the injection needle wherein, in one embodiment, the administering device includes a removing device for removing the protective cap from the injection needle and, in another embodiment, the administering device includes a needle protecting sleeve shiftable generally in alignment with the casing and generally between a front position, advanced relative to the casing, for protecting the injection needle and to a rear position, retracted relative to the casing, for inserting the injection needle into a tissue. In one embodiment, the needle protecting sleeve is prevented from moving completely into the rear position by a lock when the protective cap is protecting the injection needle.

In one particularly preferred embodiment of the present invention, a sleeve is formed as the removing device by a needle protecting sleeve of a protective means, which can be shifted along the longitudinal axis of the casing. In order to protect the injection needle, the needle protecting sleeve is attached to the casing in such a way that it completely surrounds the injection needle in a front or forward position, advanced relative to the casing, and preferably protrudes slightly beyond the injection needle in the insertion direction. The needle protecting sleeve can be shifted relative to the casing into a rear position, retracted relative to the casing, until the injection needle completely protrudes from the casing. In order to insert the injection needle into a tissue when administering an injectable product, the administering device is placed onto an insertion point on the tissue via the front end of the needle protecting sleeve in the insertion direction. In order to insert the injection needle into the tissue, the administering device is pressed against the surface of the tissue, such that the needle protecting sleeve is retracted relative to the casing. The insertion procedure can then be performed either manually or by an insertion mechanism, wherein, for example, the entire injection means can be shifted relative to the casing and, as applicable, also relative to the removing device. The injection needle remains protected from access during the entire insertion procedure. This rules out pricking injuries, the needle remains invisible and contamination of the injection needle is avoided. When the injection needle is removed from the tissue, the needle protecting sleeve is again shifted over and beyond the injection needle by a biasing element without requiring manipulation by the user.

In accordance with the first aspect of the invention, a latching means—such as the gripping arm described above—is advantageously provided on the needle protecting sleeve, such that the needle protecting sleeve can, in addition to its needle protecting function, also fulfill a protective cap removing function for removing the protective cap during the insertion procedure. No additional sleeve is then needed in order to provide the removing device in accordance with the invention.

In accordance with a second aspect of the present invention, a device for administering an injectable product comprises a casing, an injection means including an injection needle pointing in the insertion direction, a protective cap which can be placed onto the injection needle and a needle protecting sleeve. In accordance with the invention, the needle protecting sleeve can be shifted along the casing. As described above, the needle protecting sleeve is moved to a front position, advanced relative to the casing, in order to protect the injection needle, and when the needle is inserted into a tissue, can be moved to a rear position, retracted relative to the casing. In accordance with the invention, in one embodiment the needle protecting sleeve is prevented from retracting completely into the rear position for inserting the injection needle by a locking means, as long as the protective cap is still placed on the injection needle. Accordingly, the needle protecting sleeve can only be moved over a partial distance of an overall retraction distance necessary for an insertion procedure. This partial distance can be infinitesimally small or can tend towards zero. Only when the protective cap is removed can the needle protecting sleeve be moved over the overall retraction distance.

Using the locking means in accordance with the present invention, it is easily and quickly recognizable whether a protective cap is placed on the injection needle or whether it has already been removed. If the needle protecting sleeve is prevented from retracting completely into the rear position, i.e., if an insertion procedure of the injection needle into the tissue is locked or prevented, the user can immediately recognize that the protective cap has to be removed from the injection needle first.

Therefore, when the protective cap is attached, the locking means is in a locking position for the injection procedure and when protective cap is removed, the locking means is in an exposing position for the needle protecting sleeve, such that an insertion procedure can be performed.

In a preferred embodiment of the present invention, the locking means is formed by at least one locking arm which cooperates with a stopper on the needle protecting sleeve. The locking arm is preferably bendable or elastic, i.e., it can be moved to a biased position. The locking arm is arranged in such a way that it is biased by the protective cap into a position in which it forms a stopper for the needle protecting sleeve. It can, for example, be bent radially outwards with respect to the longitudinal axis of the casing. The locking arm is bent outwards until it is arranged at the same radial distance from the longitudinal axis as the stopper on the needle protecting sleeve. The stopper can, for example, be formed on the sleeve by a raised area, a step or a heel. Should the needle protecting sleeve be shifted backwards in the longitudinal direction of the casing, the stopper of the needle protecting sleeve hits the locking arm and thus prevents the sleeve from retracting further.

The locking arm is preferably arranged on a product container or a mounting for a product container, to which a needle unit, including an injection needle, is connected. When inserting a new needle unit with a new protective cap, the locking arm is therefore bent radially outwards and forms a locking means for a subsequent injection if the protective cap is not yet removed. The locking arm can, however, also be arranged on another element, fixed relative to the casing, as long as it can be moved from a locking position when the protective cap is attached and from an exposing position when the protective cap is removed.

In one particularly preferred embodiment of the present invention, the administering device comprises both a removing device for removing the protective cap and a locking means for locking an insertion procedure if a protective cap is not yet removed. The removing device is then formed by a needle protecting sleeve, as described above, comprising at least one gripping arm protruding inwards and the locking means is formed by a locking arm, biased radially outwards by the protective cap. The arrangement of the gripping arm and the locking arm are advantageously adjusted to each other such that when the needle protecting sleeve is retracted relative to the casing as far as a locking position in which a stopper of the needle protecting sleeve abuts the locking arm, the gripping arm simultaneously engages with a resistor on the protective cap. Particularly preferably, the protective cap does not yet protrude out beyond the needle protecting sleeve in the insertion direction. By advancing the needle protecting sleeve in the insertion direction, the protective cap is removed from the injection needle by the latch between the protective cap and the gripping arm of the removing device, and simultaneously the locking arm is moved radially inwards to its exposing position when the protective cap is removed from its locking position. The administering device is then ready to administer an injectable product, i.e., the protective cap of the injection needle is removed and the needle protecting sleeve can be retracted as far as an insertion position in which the injection needle protrudes from the casing into a tissue.

In a particularly preferred embodiment, three locking arms and three gripping arms are respectively provided, arranged at regular intervals around the circumference of the needle protecting sleeve or protective cap, respectively, wherein the gripping or locking arms are provided in the intermediate spaces of the locking or gripping arms, respectively.

A user of an administering device in accordance with the present invention does not have the option of removing the protective cap by hand or using other aids, which could possibly result in contamination of the injection needle, since when the protective cap is present, the needle protecting sleeve cannot be retracted over the protective cap. An administering device in accordance with the invention nonetheless enables the individual steps in administering an injectable product to be quickly and reliably performed.

DETAILED DESCRIPTION

Figure 1:
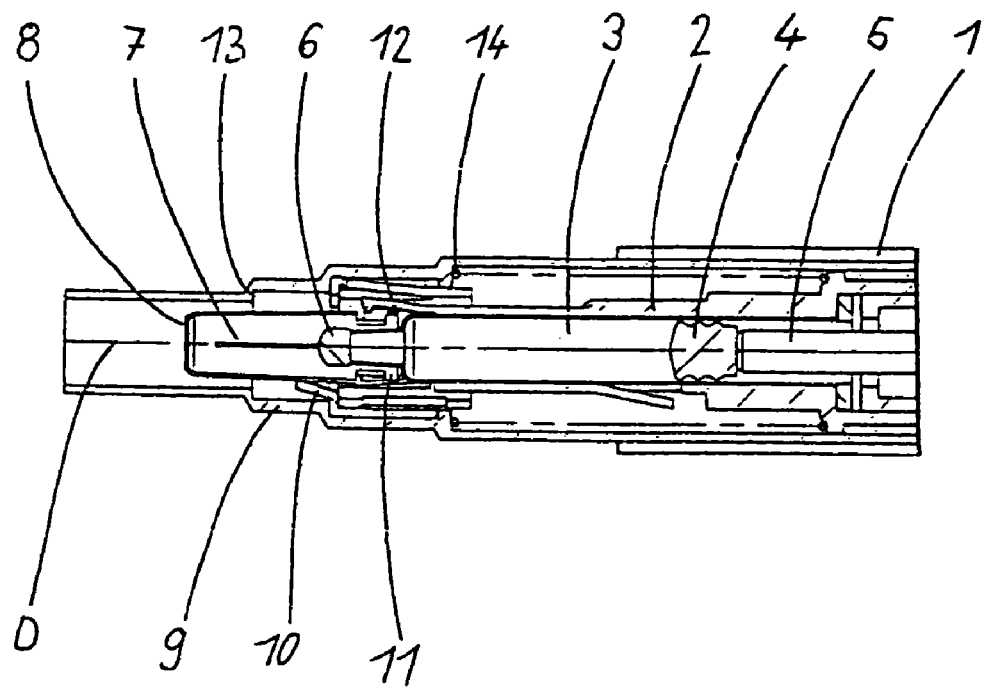
FIG. 1 is a longitudinal section through a front part of an administering device in accordance with the present invention, with a needle protecting sleeve in an advanced position and an attached protective cap.

FIG. 1 shows the front part of an administering device for an injectable product. It should be understood that the present invention may be used with any suitable administering or injection device, including those known to those skilled in the art, and that the rear part or operating mechanism of the administering device does not necessarily comprise means essential to the present invention and is therefore omitted for the benefit of clarity in the figures. It should also be understood that a suitable dosing, delivery or triggering means can, for example, be accommodated in the administering or injection device.

FIG. 1 shows a casing 1 of the administering device, in which an injection means or mechanism is accommodated. Of the injection means, FIG. 1 shows a mounting 2 for a product container 3 including a stopper 4 which can be driven by piston rod 5, and a needle unit 6 comprising an injection needle 7 which is connected to the product container 3 in the insertion direction along a longitudinal axis D of the casing 1. A protective cap 8 is placed on the needle unit 6 with the injection needle 7 in such a way that it is plugged onto a collar of the needle unit 6 by a clamp fitting. Instead of the clamp fitting, a latching connection with a low latching resistance can, for example, also be used. A needle protecting sleeve 9 is arranged such that it can be shifted within the casing 1. The needle protecting sleeve 9 can therefore also be shifted relative to the mounting 2 for the product container 3 and relative to the needle unit 6 and the protective cap 8. The front part of the needle protecting sleeve 9 protrudes beyond the protective cap 8 in the insertion direction.

The needle protecting sleeve 9 comprises a gripping arm 10 on its inner circumference. For simplification, only one gripping arm is visible in the drawing. Preferably, however, three gripping arms are arranged at regular intervals around the inner circumference (although any number of such arms may be used). The gripping arm (or arms) 10 projects obliquely inwardly generally in the insertion direction from the needle protecting sleeve 9 towards the longitudinal axis D. At its rear opening, via which it is plugged or attached onto the collar of the needle unit 6, the protective cap 8 comprises a skirt 11 which forms a resistor or stopper for the gripping arm 10. The gripping arm 10 abuts an outer circumferential area of the protective cap 8 and is bent slightly radially outwardly by it, such that the gripping arm 10 is elastically biased. A locking arm 12 is arranged on the mounting 2 for the product container 3 in the insertion direction, as an extension of the mounting 2. The locking arm 12 abuts the skirt 11 of the needle protecting cap 8 and is bent radially outwardly by it, such that the locking arm 12 is biased and its tip is arranged at a distance from the longitudinal axis D. The administering device shown in FIG. 1 is in an initial position in which it can also be stored over a long period of time.

Figure 2:
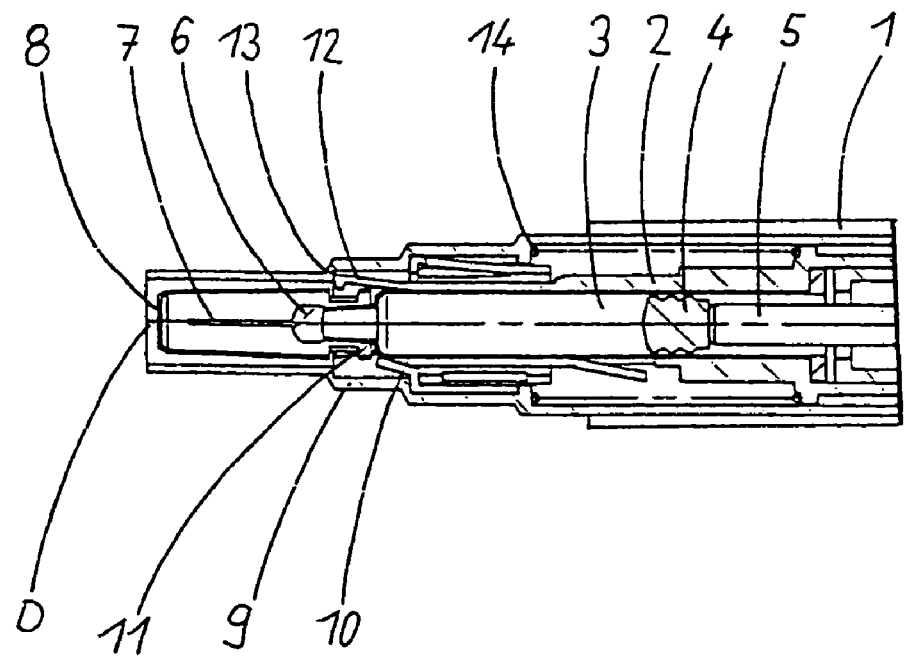
FIG. 2 is a longitudinal section through a front part of an administering device, with a needle protecting sleeve in a retracted position and an attached protective cap.

FIG. 2 shows the administering device from FIG. 1, with a needle protecting sleeve 9 which is partially retracted counter to the insertion direction, along the longitudinal axis D of the casing. The needle protecting sleeve 9 can be retracted until it hits the locking arm 12 via a step 13. The step 13 is arranged at the same radial distance from the longitudinal axis D as the foremost point of the locking arm 12 in its position bent outwards from the skirt 11 of the protective cap 8. Since the step 13 of the needle protecting sleeve 9 abuts the locking arm 12, the needle protecting sleeve is prevented from retracting further counter to the insertion direction, such that the needle protecting sleeve is in a locking position. As shown, the needle protecting sleeve 9 can preferably be retracted exactly until it just still surrounds the protective cap 8. When the needle protecting sleeve 9 is retracted, the gripping arm 10 is drawn or moved over the circumferential area of the protective cap 8. With the needle protecting sleeve 9 in the locking position, the gripping arm 10 is in a position protruding slightly beyond the skirt 11 and moves slightly radially inwards due to its bias. In this position, the tip of the gripping arm 10 lies opposite the facing area of the skirt 11 which forms a rim of the protective cap 8. When the needle protecting sleeve 9 is retracted, a spring 14 positioned between the needle protecting sleeve 9 and an element fixed relative to the casing is compressed.

The administering device from FIG. 2 is depicted in a locking or locked position. An insertion procedure of the administering device cannot yet be performed, since the protective cap 8 is still on the injection needle 7. The removing device of the administering device is, however, already in a latched position in which the gripping arm 10 is latched to the needle protecting sleeve 9 in the insertion direction.

FIG. 3 again shows the needle protecting sleeve 9 in a position pushed forward in the insertion direction relative to the casing 1. The needle protecting sleeve 9 can be advanced by the tensing force of the spring 14. When the needle protecting sleeve 9 is advanced, the gripping arm 10 is moved forward with it. Since it is latched to the protective cap 8, i.e., the foremost point of the gripping arm 10 abuts the skirt 11 of the protective cap 8, the protective cap 8 is released from its clamping connection on the collar of the needle unit 6 and removed from the needle unit 6 and the injection needle 7. During the entire procedure of removing the protective cap 8, the injection needle 7 is surrounded by the circumferential wall of the needle protecting sleeve 9, such that it is protected from access.

When the protective cap 8 is removed, the bias of the locking arm 12 is released, such that it moves generally radially inwardly relative to the longitudinal axis D. The distance between the tip of the locking arm 12 and the longitudinal axis D of the casing 1 is therefore smaller than when the locking arm 12 is biased.

Figure 3:
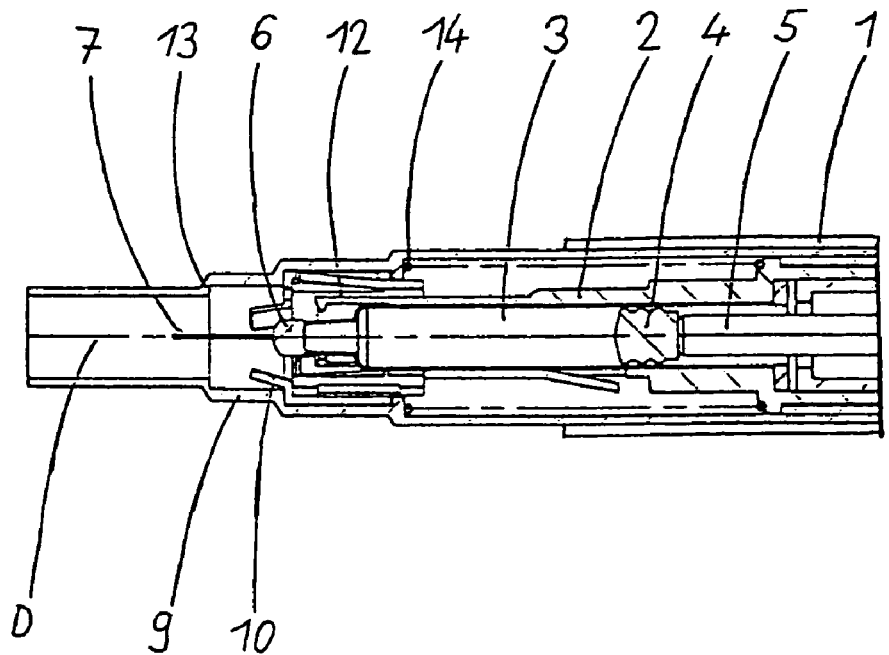
FIG. 3 is a longitudinal section through a front part of an administering device, with an advanced needle protecting sleeve and a removed protective cap.

In FIG. 3, the administering device is in an exposing position of the needle protecting sleeve 9, without a protective cap 8 around the injection needle 7, such that it is ready to administer an injectable product.

Figure 4:
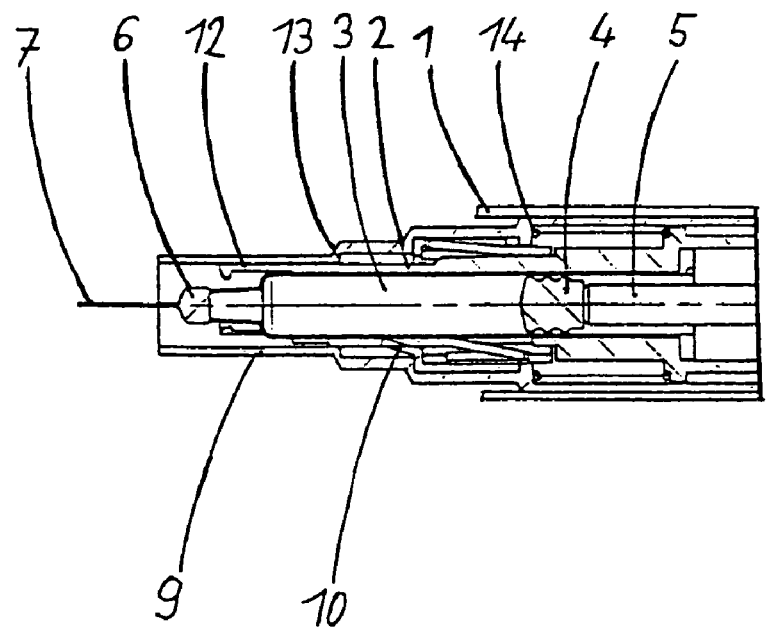
FIG. 4 is a longitudinal section through a front part of an administering device, with a retracted needle protecting sleeve and a removed protective cap.

FIG. 4 shows the administering device in an insertion position in which the injection needle 7 is inserted into a tissue (not shown). The needle protecting sleeve 9 is then in a position shifted sufficiently far backwards relative to the casing that the injection needle 7 protrudes beyond the front edge of the needle protecting sleeve 9 and can be inserted into a tissue. For inserting, the administering device—with the needle protecting sleeve 9 pushed forwards—is placed onto the tissue and then pressed substantially vertically onto the tissue, wherein the needle protecting sleeve 9 shifts backwards into the casing 1. Due to their small distance from the longitudinal axis D in the exposing position, the locking arms 12 are thus guided along the inner area of the needle protecting sleeve 9 and no longer abut the step 13 of the needle protecting sleeve 9. When the needle protecting sleeve 9 is retracted, the spring 14 is compressed, such that when the administering device is removed from the tissue, the spring 14 shifts the needle protecting sleeve 9 back into a front position in which the injection needle 7 is surrounded by the needle protecting sleeve 9. The injection needle remains inaccessible and invisible during the entire administering procedure.

The injection needle can also, for example, be inserted by an administering device comprising an insertion means which enables it to be automatically inserted. The insertion means can, for example, be triggered by the needle protecting sleeve, when the latter is in its completely retracted position. An administering device comprising such an insertion means is, for example, described in a parallel application by the Applicant entitled "Administering Device Comprising an Insertion and Delivery Means", the disclosure of which is incorporated herein by reference.

For using the administering device again, the needle unit 6 together with the injection needle 7 is removed and a new needle unit with a sterile injection needle is attached. The gripping arm 10 and the locking arm 12 are thus moved back to their biased positions, such that before administering an injectable product, the administering device is in accordance with the invention initially moved back to a locking position with an attached protective cap, in order to then be moved to an operable exposing position of the needle protecting sleeve, without a protective cap.

In the foregoing description, embodiments of the invention, including preferred embodiments, have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A device for administering an injectable product, comprising:
 a) a casing;
 b) an injection means arranged in the casing, the injection means comprising a container fluidly connected to an injection needle pointing in an insertion direction;

c) a protective cap removably mounted on the injection means for covering the injection needle; and d) a needle protecting sleeve comprising a removing device for removing the protective cap from the injection means, wherein the removing device is slaved by a movement of the needle protecting sleeve and the needle protecting sleeve is slidably coupled to the casing and movable counter to the insertion direction against a restoring force, wherein the removing device comprises at least one gripping arm disposed on an inner circumference of the protecting sleeve configured for gripping an outer circumference of the protective cap such that when the needle protecting sleeve is moved against the restoring force from an initial position, in which the gripping arm is unconnected from the protective cap, to a retracted position, in which the at least one gripping arm forms a latching connection with the outer circumference of the protective cap, the restoring force causes the at least one gripping arm to move in the insertion direction and carry the protective cap to remove the protective cap from the injection means.

2. The administering device as set forth in claim 1, wherein the gripping arm projects generally inwardly, obliquely from the needle protecting sleeve with respect to the insertion direction and engages with the outer circumference of the protective cap to remove the protective cap.

3. The administering device as set forth in claim 2, wherein the gripping arm is formed by a rim of the sleeve pointing generally inwardly into the casing.

4. The administering device as set forth in claim 1, wherein when the at least one gripping arm is in the initial position, the gripping arm abuts an outer circumferential area of the protective cap and is bent radially outwardly by the protective cap such that the gripping arm is elastically biased.

5. The administering device as set forth in claim 1, wherein when the at least one gripping arm moves into the retracted position, the gripping arm is drawn or moved over a rim at the circumferential area of the protective cap such that the gripping arm forms the latching connection with the rim.

6. A device for administering an injectable product, comprising:

a) a casing;

b) an injection means arranged in the casing, the injection means comprising a container fluidly connected to an injection needle pointing in an insertion direction;

c) a protective cap which can be releasably placed onto the injection needle; and d) a needle protecting sleeve which can be shifted along the casing generally between a front position, advanced relative to the casing, to protect the injection needle and a rear position, retracted relative to the casing, when inserting or to insert the injection needle into a tissue, the needle protecting sleeve comprising gripping arms slaved by a shifting movement of the needle protecting sleeve; wherein e) when the protective cap is in place, the needle protecting sleeve is prevented from retracting completely into the rear position by a locking means;

f) the locking means comprising a locking arm extending obliquely from the casing for abutting a step arranged on the needle protecting sleeve and upon moving the needle protecting sleeve from the front position, the locking arm and the step abut at a locking position and prevent the needle protecting sleeve from moving to the rear position;

g) when the protecting sleeve is in the locking position, the gripping arms latch with a circumferential rim of the protective cap, and when the needle protecting sleeve is moved from the locking position to the front position, the gripping arms carry the protective cap and release the cap from the injection needle; and h) upon releasing the cap from the injection needle, the locking arms extend radially inwardly from the casing such that when the needle protecting sleeve is moved from the front position to the rear position, the locking arms are guided along an inner area of the needle protecting sleeve and do not engage with the step.

7. The administering device as set forth in claim 6, wherein the locking arm comprises at least one bendable locking arm arranged within the casing, said at least one bendable arm bent generally toward the needle protecting sleeve by the protective cap.

8. The administering device as set forth in claim 7, wherein the at least one locking arm is bent generally radially outward with respect to a longitudinal axis of the casing by the protective cap and forms a stopper for the needle protecting sleeve when it is retracted.

9. The administering device as set forth in claim 6, wherein upon the needle protecting sleeve reaching the rear position, the needle protecting sleeve is shifted to the front position where the injection needle is surrounded by the needle protecting sleeve.

10. The administering device as set forth in claim 9, wherein the needle protecting sleeve is moved into the rear position against a biasing force of a spring, and the biasing force moves the needle protecting sleeve to the front position.

11. The administering device as set forth in claim 6, wherein the locking means is in an exposing position for the needle protecting sleeve when the protective cap is removed.

12. The administering device as set forth in claim 6, wherein the locking means projects from a product container or from a mounting for a product container generally toward the injection needle.

13. The administering device as set forth in claim 6, wherein the step is formed by a rim of the sleeve pointing generally inwardly into the casing.

14. The administering device as set forth in claim 6, wherein the sleeve can be moved in the insertion direction along the longitudinal axis of the casing, manually or by a biasing element to remove the protective cap.

* * * * *